(12) United States Patent
Petersen

(10) Patent No.: US 8,747,457 B2
(45) Date of Patent: Jun. 10, 2014

(54) MEDICAL DEVICE AND METHOD OF MANUFACTURING SAME

(75) Inventor: Jesper Schade Petersen, Holmegaard (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/849,459

(22) Filed: Aug. 3, 2010

(65) Prior Publication Data

US 2011/0040368 A1    Feb. 17, 2011

(30) Foreign Application Priority Data

Aug. 11, 2009  (GB) .................................. 0914044.3

(51) Int. Cl.
*A61F 2/06* (2013.01)

(52) U.S. Cl.
USPC .......................... 623/1.36; 623/1.13; 623/1.14

(58) Field of Classification Search
USPC ....................................... 623/1.13, 1.14, 1.36
See application file for complete search history.

(56) References Cited

U.S. PATENT DOCUMENTS

| 5,720,776 | A  | * | 2/1998  | Chuter et al. ................. 623/1.36 |
| 5,891,193 | A  |   | 4/1999  | Robinson et al. |
| 5,961,546 | A  |   | 10/1999 | Robinson et al. |
| 6,355,061 | B1 | * | 3/2002  | Quiachon et al. ............ 623/1.36 |
| 6,451,048 | B1 |   | 9/2002  | Berg et al. |
| 6,814,748 | B1 | * | 11/2004 | Baker et al. .................. 623/1.14 |
| 6,860,901 | B1 |   | 3/2005  | Baker et al. |
| 7,081,132 | B2 | * | 7/2006  | Cook et al. ................... 623/1.36 |
| 2004/0117004 | A1 | * | 6/2004  | Osborne et al. .............. 623/1.36 |
| 2005/0159803 | A1 | * | 7/2005  | Lad et al. ..................... 623/1.13 |
| 2005/0159804 | A1 |   | 7/2005  | Lad et al. |
| 2005/0240259 | A1 |   | 10/2005 | Sisken et al. |
| 2007/0100432 | A1 |   | 5/2007  | Case et al. |
| 2008/0033534 | A1 |   | 2/2008  | Cook et al. |
| 2008/0082159 | A1 | * | 4/2008  | Tseng et al. ................. 623/1.13 |
| 2009/0171442 | A1 | * | 7/2009  | Young et al. ................. 623/1.15 |
| 2010/0057195 | A1 | * | 3/2010  | Roeder et al. ................ 623/1.35 |

FOREIGN PATENT DOCUMENTS

| EP |      0579523 | A1 | 1/1994 |
| WO |      9639999 | A1 | 12/1996 |
| WO |   2005072652 | A1 | 8/2005 |
| WO | PCT/US2010/044242 |  | 11/2010 |

* cited by examiner

*Primary Examiner* — Kathleen Holwerda
*Assistant Examiner* — Sarah W Aleman
(74) *Attorney, Agent, or Firm* — Brinks Gilson & Lione

(57) ABSTRACT

A stent (10) has wrapped therearound a barb element (12) formed of a length of wire provided with first and second ends (14, 16) forming barb prongs. In intermediate zone (22), the barb element (12) is wrapped or coiled. The two pronged ends (14, 16) extend out of the graft element (26) to provide an anchoring function to the medical device. As well as being wrapped onto a strut of the stent (10), the barb element (12) is sutured to the stent (10) and to the graft material (26) by suture stitching (28). The turns of the coiling or wrapping in section (22) assist in fixing the barb element (12) relative to the suture (28) and thus to the stent graft (24). The barb elements (12) could be made of any suitable material, including Nitinol. This structure of barb elements provides an effective arrangement which is easy to manufacture, which provides strong barbs able to withstand the high processing temperatures required for setting shape memory elements of the device.

9 Claims, 2 Drawing Sheets

MEDICAL DEVICE AND METHOD OF MANUFACTURING SAME

TECHNICAL FIELD

The present invention relates to a medical device including one or more barbs and to a method of manufacturing such a medical device.

BACKGROUND OF THE INVENTION

It is common to provide medical devices designed to be implanted in the vasculature of a patient with one or more barbs for securing the medical device in position within the vessel and for ensuring that the medical device does not migrate over time. The barbs are typically pin-like elements which are able to penetrate into the tissue of the wall of the vessel so as to anchor the medical device in place.

There are primarily two methods of providing barbs on such medical devices. The first is to provide the barbs integrally with the stent or stents of the medical device. The second connects the barb or barbs to a graft element of the medical device, typically by suturing. With the first option, where the barbs are integral with a stent of the device, the barbs benefit from support of the stent and thus have enhanced rigidity and function. With this option, the barbs can either be integrally formed with the stent or fixed to the stent in a subsequent procedure. For instance, a barb may be formed by cutting a part of a stent structure to create the pin-like element of the barb. This may, for instance, be by means of laser cutting, which is a well-known method for making stents, particularly Nitinol stents. While this method provides a satisfactory barb structure fully supported by the stent, this method of manufacture is expensive. It also requires careful handling of the stent after its formation as the barb or barbs present an enhanced risk of snagging of the stent during subsequent manufacturing and handling procedures.

Another method of fixing the barb or barbs to a stent structure involves soldering or otherwise bonding the barb or barbs to the stent. This is suitable for stents made of similar materials, such as stainless steel, but is not suitable for materials which require subsequent treatment at high temperatures. For instance, barbs cannot be soldered or otherwise bonded to a Nitinol stent as such stents require subsequent heat treatment at very high temperatures (in the region of 500° C.) for shape memory setting.

With respect to the second method of coupling the barbs to a medical device, that is by suturing the barb to graft material of the device, this provides the ability to fit the barbs at a relatively late stage in the assembly or manufacture of the device. It is generally considered that such barbs should be sutured to the graft material in such a manner that the barbs cannot rub against any other hard structure of the medical device, such as any other barb or any stent of the device. Any rubbing of this nature can cause greater wear of the graft material and risks premature tear of the graft material and thus premature failure of the medical device. In addition to this, this method of attaching such barbs to the medical device involves additional and time consuming manufacturing steps.

SUMMARY OF THE INVENTION

The present invention seeks to provide an improved method of forming an implantable medical device, such as a stent graft, and an improved medical device including one or more barbs.

According to an aspect of the present invention, there is provided a method of forming an implantable medical device, including the steps of providing a graft member, providing at least one stent attached to the graft member; providing at least one barb element; wherein the barb element is mechanically coupled to the stent and sutured in position by means of a suture between the barb element, the stent and the graft member.

This arrangement provides a medical device with one or more barbs fitted to the device and in particular coupled mechanically to the stents so as to benefit from direct support from the stent. The barb is sutured to the device, which can be achieved by a relatively simple assembly process after the construction of the majority of the medical device.

In the preferred embodiment, the barb element is mechanically coupled to the stent by being wrapped around a portion of the stent. Wrapping of the barb element provides a strong mechanical link between the stent and the barb and one which can be achieved relatively simply during the assembly procedure.

Advantageously, the barb element is fitted after coupling of the stent to the graft member. In the preferred embodiment, the barb element is fitted towards the very end of the assembly procedure. Thus, the device during assembly can be substantially free of barbs, which makes it much easier to handle.

In the preferred embodiment, the barb element is formed in a coiled or wrapped configuration prior to fitting of the stent and graft member. In practice, the barb element would be opened slightly for fitting onto the stent and would then preferably spring back to its original wrapped or coiled configuration after having been fitted to the stent.

Advantageously, the barb element is fitted to the stent and graft member by a single suture tie. This is a simple procedure and provides, where the barb element is coiled or wrapped, an effective coupling arrangement of the barb to the stent and graft member. In the preferred embodiment, the coiling or wrapping of the barb element provides a strong mechanical coupling to the stent, while the suture prevents a barb element sliding along the stent.

Advantageously, the barb element is provided with two barb prongs, the prongs being at either end of said barb element. Thus, a single barb can provide two piercing prongs and thus greater anchoring function than conventional barbs.

Advantageously, the barb element is formed of a shape memory material, such as Nitinol. Shape memory materials, particularly Nitinol, are generally very strong and thus particularly suited for barb elements. Moreover, providing a barb element of shape memory material enables the use of shape memory characteristics in the deployment of the medical device.

It will be appreciated that in the preferred embodiment, the medical device will be provided with a plurality of barb elements fitted to the device.

This method is particularly suited for the manufacture of stent grafts, such as those formed of one or more tubular graft elements with one or stents fitted to the graft elements and a plurality of barbs fitted to at least one stent element of the stent graft.

According to another aspect of the present invention, there is provided an implantable medical device including a graft member; at least one stent attached to the graft member and at least one barb element; wherein the barb element is mechanically coupled to the stent and sutured in position by means of a suture between the barb element, the stent and graft member. The implantable medical device may be a stent graft, a vena cava filter, occlusion device or any other implantable medical device.

According to another aspect of the present invention, there is provided a barb element for an implantable medical device, the barb element being in the form of an elongate member having first and second ends; said first and ends providing first and second barb prongs; and including in a region of the barb element between said first and second ends a coiled or wrapped portion.

BRIEF DESCRIPTION OF THE DRAWING

Embodiments of the present invention are described below, by way of example only, with reference to the accompanying drawings, in which.

DETAILED DESCRIPTION

Figure 1:
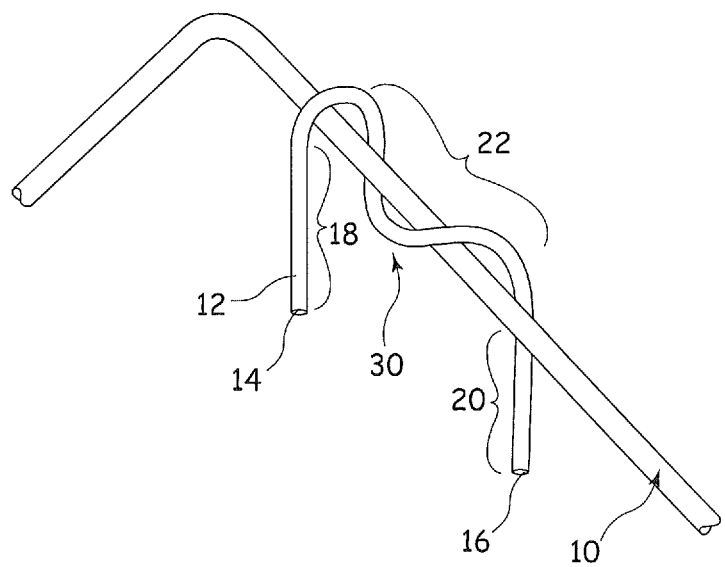
FIG. 1 is a perspective view of a part of a stent provided with a barb element fitted thereto, in accordance with an embodiment of the present invention.

Referring to FIG. 1, there is shown a part of a stent 10, which in this embodiment has a zig-zag form well known in the art. Wrapped around a strut of the stent 10 is a barb element 12. In this embodiment, the barb element 12 is formed of a length of wire provided with first and second ends 14, 16 to form barb prongs, that is elements which in use will pierce into the wall of a body vessel. The prong elements 14, 16 form part of straight or relatively straight portions 18 and 20, respectively, of the barb element 12 and preferably are substantially parallel to one another, as shown in particular in FIGS. 1 and 2. As will be apparent from the disclosure below, arranging the prongs 14, 16 to extend substantially in the same direction assists in the assembly of the barb element 12 to the medical device and also provides barb prongs which will provide complimentary fixing anchors. In other words, the anchors will work together in an additive manner as two distinct barbs.

In intermediate zone 22, which in this embodiment is at the centre of the wire forming the barb element 22, the barb element 12 is wrapped or coiled, in this case for one and a half turns. FIG. 1 depicts the barb element 12 being relatively loosely wrapped over the strut of the stent 10, but in the preferred embodiment this wrapping will be relatively tight, it being shown loose solely for the purposes of clarity.

Figure 2:
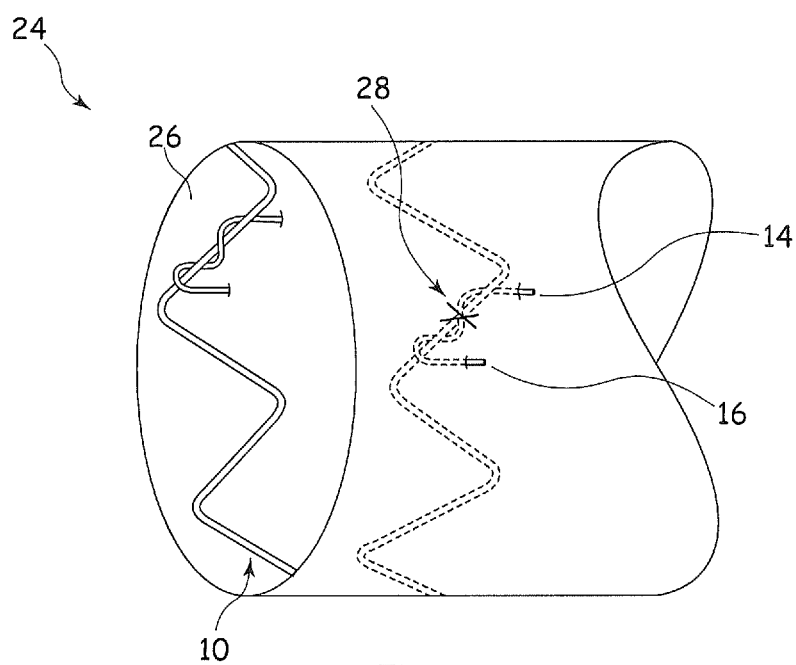
FIG. 2 shows an end of a stent graft including a stent and barb element in accordance with an embodiment of the present invention.

Referring now to FIG. 2, there is showing the distal end of a stent graft 24, which is provided with a plurality of barb elements 12 of the type shown in FIG. 1. The stent graft 24 includes, in this embodiment, a tubular graft element 26 to which there are attached, in a conventional manner, a plurality of stents 10. In this embodiment, barb elements 12 are coupled to the most proximal stent 10 of the stent graft 24, although the barb elements could be provided at any desired position along the stent grafts 24.

As can be seen in FIG. 2, the barb element 12 is wrapped around the stent 10, in the manner shown in FIG. 1, and its two pronged ends 14, 16 extend out of the graft element 26, that is radially out from the tubular portion of the stent graft 24. This is achieved by causing the pronged ends 14, 16 to pierce through the graft material 26 of the stent graft 24. It is preferred that the pronged elements 14, 16 extend also in a distal direction of the stent graft 24 (or other implantable medical device to which they are attached), so as to provide an anchoring function to counter any effects of migration of the implantable medical device caused by the force of fluid flow within the vessel.

As well as being wrapped onto a strut of the stent 10, the barb element 12 is sutured to the stent 10 and to the graft material 26 by suture stitching 28, which in the preferred embodiment is a single stitch, loop or tie. Advantageously, this suture 28 is located, in this embodiment, at the centre point of the barb element 12 and just where the coiled portion 22 begins its second wrap around the stent 10, that is at location 30 shown in FIG. 1. The suture 28 could be positioned in any location along the coiled or wrapped section 22 of the barb element 12. The turns of the coiling or wrapping in section 22 will assist in fixing the barb element 12 relative to the suture 28 and thus to the stent graft 24.

The barb element 12 could be made of any suitable material, including steel or other metal or alloy but is preferably made of a shape memory material, most preferably of a shape memory alloy such as Nitinol. Barbs made of a shape memory metal or alloy such as Nitinol can be particularly strong and also will have shape memory characteristics assisting in their fitting to an introducer with the stent graft 24 and their deployment within a vessel of a patient. For instance, the barb elements 12 could be compressed and allowed to regain their shape memory characteristics in situ in the patient. In this latter circumstance, the shape memory characteristics of the barb elements 12 are preferably such as to ensure tight wrapping of the barb elements 12 to their associated stent 10 and correct orientation of the pronged elements 14, 16 once these are deployed.

In the preferred embodiment, the barb elements 12 are fitted to the stent or stent 10 after the stent or stents have been fitted to the graft element 26. In particular, stent 10 may be sutured, bonded or otherwise attached to the graft material 26 and once this have been achieved, the barb elements are then fitted to the stent. In this regard, the barb elements 12 would already be provided in the coiled configuration shown in FIG. 1, in which case the barb elements 12 would be slightly opened, by twisting, and fitted onto the stent 10, in this embodiment from inside the graft element 26, and then pushed through the graft material 26 in a radially outward direction until the pronged elements 14, 16 pierce the graft material and the coiled zone 22 comes into abutment with the strut of the stent 10. It will appreciated that the strut of the stent 10 could be used to assist in the opening out of the barb element 12 for the fitting procedure, by providing a coil opening surface.

Once the barb element 12 has been fitted to the stent 10, the suture 28 is made by conventional threading or tying. The suture 28 passes around the strut of the stent 10, the barb element 12 and the graft material 26.

It is to be understood that in place of a suture 28, there could be provided another means of coupling of the barb element 12 to the stent 10 and graft material 26, such as bonding or the like. However, a suture 28 is the preferred arrangement.

It will be appreciated that barb elements 12 can be easily fitted to the stent graft 24 during the manufacture process in a manner which is simple, reliable and efficient.

This fitting of the barb element 12, that is by a mechanical coupling to the stent 10 and a suture to the graft element 26, provides a solid fixing of the barb element 12 to the stent graft 24 and one in which the barb element 12 can rely upon the support of the stent 10 to provide a strong anchoring function. Moreover, the connection to the graft tubing 26 ensures that the barb element 12 retains its position and prevents any appreciable movement of the barb element 12 relative to the stent 10, thereby minimising the chance of premature wear of the stent graft 24 of the type sought to be avoided by prior art devices.

The fitting arrangement is suitable both for balloon and self-expandable stents, the latter benefiting from the ability to treat the medical device at the high temperatures required for setting shape memory alloys. Moreover, the use of a shape memory material to make the barbs 12 can enhance their coupling to the stent 10 by relying upon the shape memory effect, which can provide a continuous tightening force around the strut of the stent 10 during the life of the stent graft 24 or other medical device to which the barb is fitted.

Figure 3:
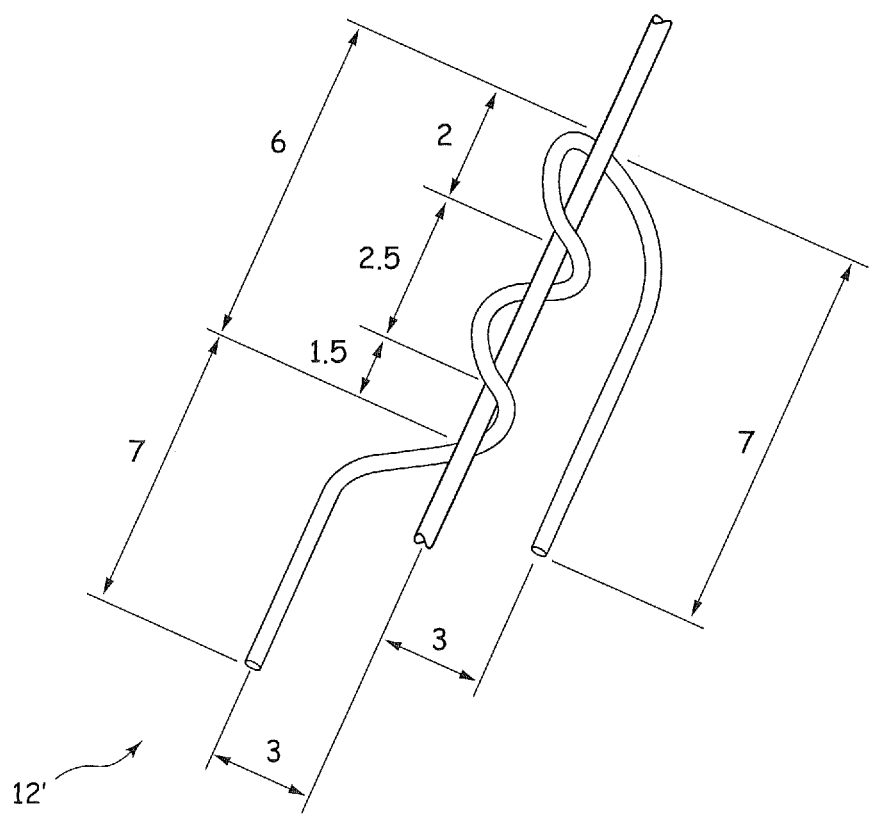
FIG. 3 shows another embodiment of barb element.

FIG. 3 shows an embodiment of barb element 12 which may be suitable for an aortic stent graft or other implantable medical device fitted within the aortic artery of a patient. It is to be appreciated that the dimensions of the barb element shown in FIG. 3 are appropriate for a particular medical application and that in other applications the barb element may have different dimensions.

In the embodiment of FIG. 3, each pronged element has a length of around 7 mm, whereas the coiled or wrapped section of the barbed element 12' has an overall length of around 6 mm. This is formed by a whole turn section of around 2.5 mm and two end sections of around 1.5-2 mm respectively. The prongs of the barb element 12' are preferably spaced about 3 mm from the strut of the stent 10 and point substantially in the same direction. The pronged elements are substantially straight in this embodiment.

It will be appreciated that the pronged elements 14, 16 of the barb 12 need not be straight and could have a slight curvature. They also need not extend in the same direction as one another. In some embodiments, it may be desired to have pronged ends, thus barb elements, which extend in different directions to give different anchoring characteristics to the medical device.

What is claimed is:

1. An implantable medical device including:
   a graft member;
   at least one stent attached to the graft member and at least one separate barb element, the barb element having at least one barb end and a wrapped portion;
   wherein the barb element is mechanically coupled to the stent only by being wrapped around a portion of the stent without additional bonding and is sutured in position by means of a suture between the barb element, the stent and the graft member, the suture passing around the stent, the barb element wrapped portion and the graft member, and wherein the barb is fixed relative to the stent and the graft such that the barb is prevented from sliding on the stent.

2. An implantable medical device according to claim 1, wherein the barb element is coiled around the stent.

3. An implantable medical device according to claim 1, wherein the barb element is fitted to the stent and graft member by a single suture tie.

4. An implantable medical device according to claim 1, wherein the barb element is provided with two barb prongs, said barb prongs being at either end of said element.

5. An implantable medical device according to claim 1, wherein the barb element is formed from a shape memory material.

6. An implantable medical device according to claim 5, wherein the barb element is formed of Nitinol.

7. An implantable medical device according to claim 1, including a plurality of barb elements fitted to said stent.

8. An implantable medical device according to claim 1, wherein the device is a stent-graft.

9. An implantable medical device including:
   a graft member having an internal surface and an external surface;
   at least one stent attached to the graft member internal surface and at least one separate barb element having a first end and a second end;
   wherein the barb element is mechanically coupled to the stent only by being wrapped around a portion of the stent without additional bonding and is sutured in position by means of a suture between the barb element, the stent and the graft member, the suture passing around the stent, the barb element and the graft member, and wherein the barb is fixed relative to the stent and the graft such that the barb is prevented from sliding on the stent; and
   wherein both of the first and second ends protrude through the graft member from the internal surface to the external surface and extend radially out from the external surface and in a distal direction.

\* \* \* \* \*